(12) United States Patent
Contant

(10) Patent No.: US 9,198,605 B2
(45) Date of Patent: Dec. 1, 2015

(54) EATING UTENSIL TO MONITOR AND REGULATE DIETARY INTAKE

(76) Inventor: Christine Contant, Redmond, WA (US)

( * ) Notice: Subject to any disclaimer, the term of this patent is extended or adjusted under 35 U.S.C. 154(b) by 1391 days.

(21) Appl. No.: 12/408,622

(22) Filed: Mar. 20, 2009

(65) Prior Publication Data
US 2010/0240962 A1    Sep. 23, 2010

(51) Int. Cl.
  *A61B 5/00*   (2006.01)
  *A61B 5/11*   (2006.01)
  *A47G 21/02*  (2006.01)

(52) U.S. Cl.
  CPC .............. *A61B 5/1118* (2013.01); *A47G 21/02* (2013.01); *A61B 2562/0219* (2013.01); *A61B 2562/0247* (2013.01)

(58) Field of Classification Search
  USPC .................................. 600/300–301; 128/897
  See application file for complete search history.

(56) References Cited

U.S. PATENT DOCUMENTS

| | | | |
|---|---|---|---|
| 4,975,682 A * | 12/1990 | Kerr et al. .................. | 340/573.1 |
| 5,299,356 A | 4/1994 | Maxwell, III | |
| 5,398,688 A | 3/1995 | Laniado | |
| 5,421,089 A * | 6/1995 | Dubus et al. ................... | 30/142 |
| 5,913,310 A * | 6/1999 | Brown ......................... | 128/897 |
| 6,302,789 B2 | 10/2001 | Harada et al. | |
| 7,429,125 B2 * | 9/2008 | Sharma et al. ................ | 374/31 |
| 7,855,936 B2 * | 12/2010 | Czarnek et al. ............... | 368/10 |
| 7,914,468 B2 * | 3/2011 | Shalon et al. ................ | 600/590 |
| 7,959,567 B2 * | 6/2011 | Stivoric et al. ............... | 600/300 |
| 8,310,368 B2 * | 11/2012 | Hoover et al. ............... | 340/573.1 |
| 2001/0049470 A1 | 12/2001 | Mault et al. | |
| 2003/0009202 A1 | 1/2003 | Levine | |
| 2003/0208113 A1 * | 11/2003 | Mault et al. ................... | 600/316 |
| 2006/0087831 A1 | 4/2006 | Kramer | |
| 2006/0122474 A1 * | 6/2006 | Teller et al. ................... | 600/300 |
| 2007/0098856 A1 | 5/2007 | LePine | |
| 2007/0299321 A1 * | 12/2007 | Brown ......................... | 600/300 |
| 2008/0137486 A1 | 6/2008 | Czarenk et al. | |
| 2008/0146890 A1 * | 6/2008 | LeBoeuf et al. .............. | 600/300 |
| 2008/0146892 A1 * | 6/2008 | LeBoeuf et al. .............. | 600/300 |
| 2008/0276461 A1 | 11/2008 | Gold | |
| 2009/0048493 A1 * | 2/2009 | James et al. ................... | 600/300 |
| 2009/0177068 A1 * | 7/2009 | Stivoric et al. ............... | 600/365 |
| 2010/0125181 A1 * | 5/2010 | Hyde et al. ................... | 600/300 |
| 2014/0349257 A1 * | 11/2014 | Connor ......................... | 434/127 |

FOREIGN PATENT DOCUMENTS

| | | |
|---|---|---|
| EP | 1136035 | 1/2006 |
| JP | 2004113315 | 4/2004 |
| JP | 2006239272 | 9/2006 |
| JP | 2006252150 | 9/2006 |
| JP | 2008310606 | 12/2008 |
| KR | 10-2002-0091998 | 12/2002 |

OTHER PUBLICATIONS

"International Search Report", Mailed Date: Nov. 16, 2010, Application No. PCT/US2010/028012, Filed Date: Mar. 19, 2010, pp. 12.

* cited by examiner

*Primary Examiner* — William Thomson
*Assistant Examiner* — Bobby Soriano
(74) *Attorney, Agent, or Firm* — Payam Moradian

(57) ABSTRACT

Dietary intake regulating devices that can assist a user in measuring his or her dietary intake and optionally his or her physical activity are disclosed.

22 Claims, 6 Drawing Sheets

EATING UTENSIL TO MONITOR AND REGULATE DIETARY INTAKE

FIELD OF THE INVENTION

This invention relates generally to dietary intake regulating devices and more specifically to dietary intake regulating devices that can assist a user in measuring his or her dietary intake and optionally his or her physical activity.

BACKGROUND OF THE INVENTION

Over the past twenty years there has been a dramatic increase in the occurrence of obesity in the United States and other countries around the world. This increase in obesity has occurred even as improved approaches to weight control have been developed. The Centers for Disease Control and Prevention ("CDC") has recently estimated that the prevalence of obesity in the United States is about thirty-four percent. Obesity is a significant health problem and has been shown to be causative of or associated with a number of serious health conditions, including diabetes and heart disease.

Various devices for modifying eating behavior to assist in weight control have been reported. Dubus et al., U.S. Pat. No. 5,421,089 discloses a device with a timer that can be programmed to emit signals at predetermined intervals to help a user regulate his or her eating speed. However, the device is not capable of measuring the actual bites of food taken by a user. LePine, US Patent Application Publication No. US 2007/0098856 A1 discloses a chewing and swallowing measuring device. However, it provides little practical guidance on how the device does this and the device is not capable of measuring the actual bites of food taken by a user. Gold, US Patent Application Publication No. US 2008/0276461 A1 discloses a device that measures bites of food taken by a user using a pressure sensor that detects the weight of food. However, the ability of the pressure sensor of the device to distinguish between the weight of the food and other sources of pressure is unclear.

Therefore, there is a need for new approaches and devices to assist in weight control.

SUMMARY OF THE INVENTION

Dietary intake regulating devices that can assist a user in measuring his or her dietary intake and optionally his or her physical activity are disclosed.

In one embodiment, the dietary intake regulating device comprises an enclosure and one or more extensions. Both the enclosure and the extensions include various types of sensors for detecting different parameters such as touch sensors, stretch sensors, motion sensors, pressure sensors, photo sensors and the like. In combination, the various sensors can be used to determine the user's dietary intake and, in certain embodiments, the user's activity and non-activity levels and, if desired, their equivalence in calories. The two basic types of extensions that can be used with the enclosure are dietary intake meter extensions for measuring calories and fat consumed and activity and non-activity meter extensions for measuring calories and fat burned and non-activity behaviors. The enclosure can be configured to accept any type of extension that measures the user's dietary intake, the user's activity or non-activity levels or both, and/or provides their equivalence in calories, including multiple extensions sourced from third parties that measure the number of calories consumed and burned and the non-activity behaviors. The dietary intake regulating device can also be used as an on-the-fly calorie balance tracking device that alerts the user at any time of the day if he or she is in positive or negative caloric balance and therefore encourages the user to reduce his or her dietary intake or augment his or her physical activity. If desired, the dietary intake regulating device can be made partially or entirely waterproof to prevent damage to electrical components that could occur, for example, when washing or cleaning the device.

In one aspect of the present invention, the dietary intake regulating device is configured to detect primarily the user's bite and secondarily the user's dietary intake. Various procedures can be used for detecting the user's bite, including movement of the food, lip touch, luminosity and the like. By measuring bite, the dietary intake regulating device guides the user in pacing his or her eating speed by monitoring and regulating the elapsed time between two bites and spreading a meal over a pre-defined time period in order to allow the user to feel satiated. Optionally, the dietary intake regulating device can be configured to count the number of bites taken during a meal or snack and estimate the number of calories consumed during the meal or snack.

In another aspect of the present invention, the dietary intake regulating device is configured to measure the user's activity and non-activity levels in addition to bite and dietary intake. Various body motion sensors can be included in the device to measure activity, such as the number of steps or strides taken and walking/running distance, or non-activity, such as resting, napping and sleeping. Optionally, the dietary intake regulating device can be configured to calculate the number of calories burned during physical activity or to assign positive or negative caloric values based on non-activity behaviors.

By measuring calories consumed during a meal or snack and burned during physical activity and by assigning positive or negative caloric values based on non-activity behaviors, the dietary intake regulating device can assist the user in developing and maintaining good eating, physical activity and resting habits.

BRIEF DESCRIPTION OF THE DRAWINGS

Preferred and alternative embodiments of the present invention are described in detail below with reference to the following drawings. These depict particular embodiments of the invention and are not intended to limit the scope of the invention as set forth in the claims. All of the drawings are schematics rather than precise representations and are not drawn to scale.

DETAILED DESCRIPTION OF THE PREFERRED EMBODIMENTS

Figure 1A:
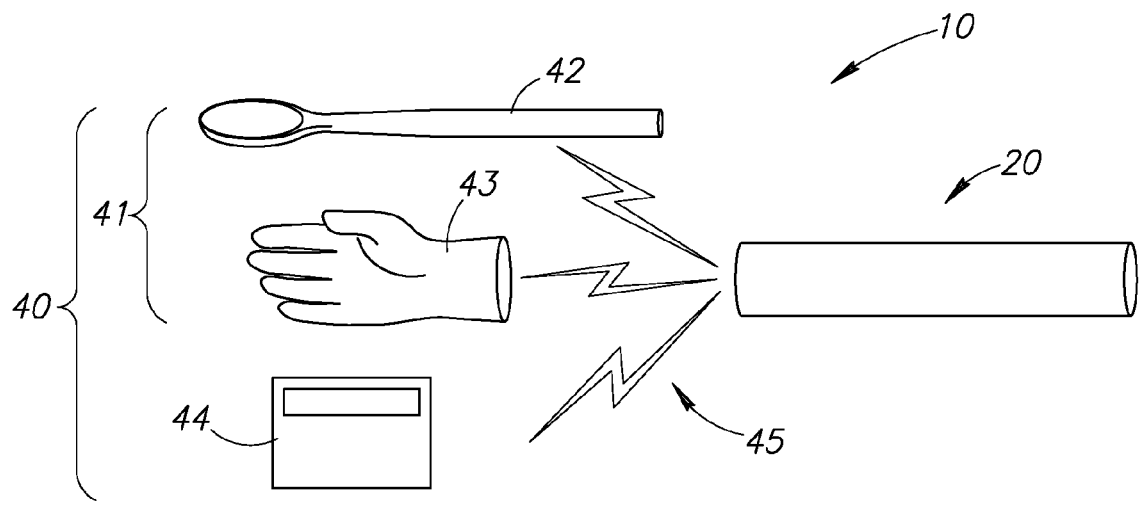
FIGS. 1A 1B are schematic representations illustrating various exemplary configurations of a dietary intake regulating device, in accordance with the present invention.
Figure 1B:
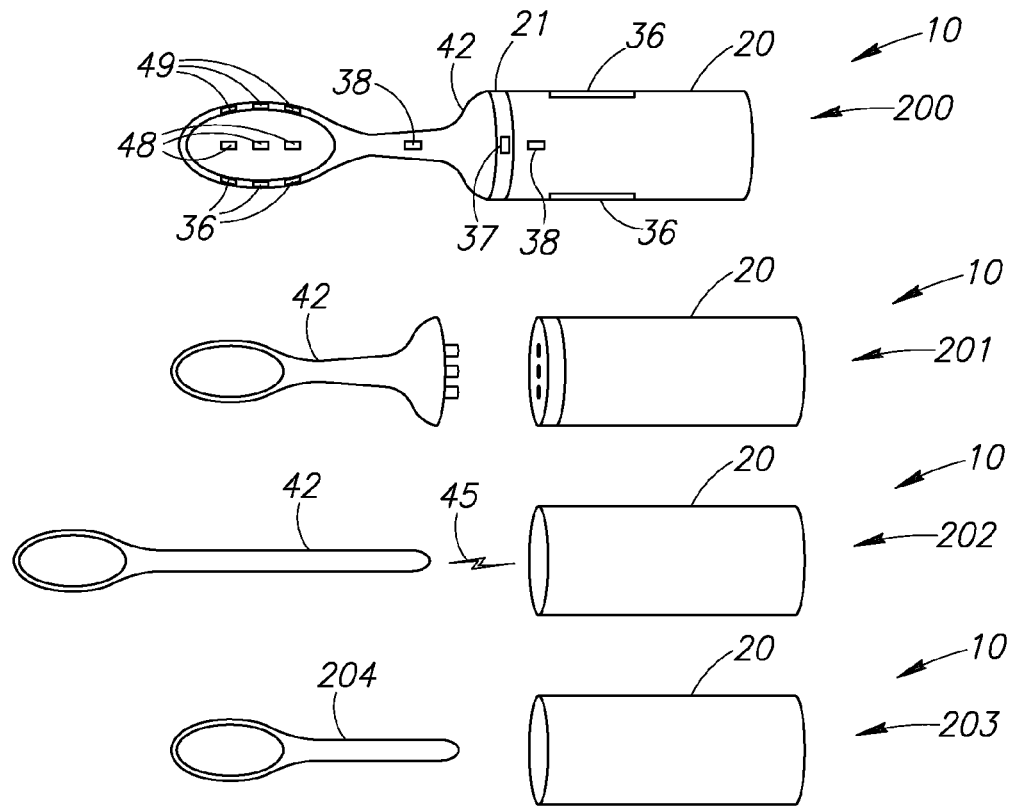
Figure 2:
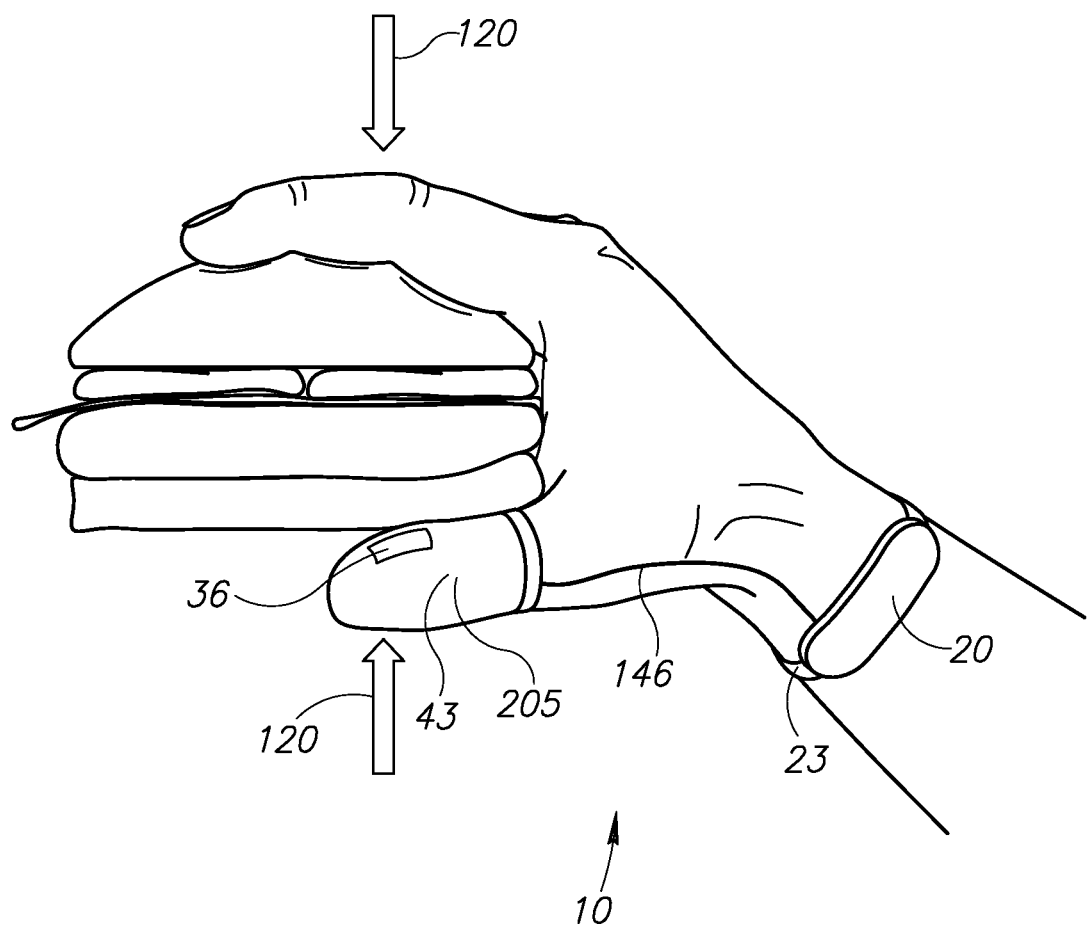
FIG. 2 is a schematic representation of an alternate embodiment of a dietary intake regulating device, in accordance with the present invention.

Referring now to FIGS. 1B and 2, schematic representations illustrating various configurations of a dietary intake regulating device 10, in accordance with embodiments of the present invention, are shown. The dietary intake regulating device 10 includes one or more electric circuits 11 (FIGS. 4, 5 and 6) wherein at least one of the electrical circuits 11 (FIG. 4) comprises a processor unit 24 that is electrically coupled to a control panel 28, a memory unit 32 and a user-utensil interface 30, and wherein, if the dietary intake regulating device 10 includes two or more electric circuits 11, each electric circuit 11 communicates either by being electrically coupled with another electric circuit 11 or by using a data link unit 26 (FIGS. 4, 5 and 6) that is configured to exchange analog or digital signals using wired or wireless communication with the other electric circuits 11, or both. The dietary intake regulating device 10 furthermore includes a set of sensors (FIGS. 1B (top panel), 4, 5 and 6) comprising one or more sensors that are configured with the processor unit 24 to detect bites of food taken by a user and that are electrically coupled to one or more of the electric circuits 11. In the embodiment illustrated in FIG. 1B, top panel, the set of sensors includes one or more pressure sensors 36, stretch sensors 37, motion sensors 38, touch sensors 48 and photo sensors 49. The dietary intake regulating device 10 furthermore includes one or more battery units 34 (FIGS. 4, 5 and 6) for providing power to the electric circuits 11. The dietary intake regulating device 10 includes a portion configured as a food carrier (see exemplary components 42 and 43 of FIGS. 1B and 2) and another portion configured as a non-food carrier (see exemplary component 20 of FIGS. 1B and 2). The electric circuits 11 are located in the food carrier portion, the non-food carrier portion, or both. The dietary intake regulating device 10 may have analog or digital signal links to other electric circuits 11, a remote station 50 (FIG. 6), a third party device 60 (FIG. 7) or any desired combination thereof.

In the embodiment illustrated in FIGS. 1A and 1B, the dietary intake regulating device 10 of the present invention is configured to include an enclosure 20 and an extension 40. This embodiment containing the enclosure 20 and the extension 40 is sometimes referred to herein as a dietary intake and activity meter platform, since it can be configured to determine the user's dietary intake and, in certain embodiments, the user's activity or non-activity levels and, if desired, their equivalence in calories. In one such embodiment, the electric circuit 11 of the dietary intake regulating device 10 containing the processor unit 24 is included in the enclosure 20 and the other electric circuits 11 of the dietary intake regulating device 10 are included in the extension 40. If desired, third party extensions 52 (FIG. 7) such as dietary intake meter extensions and activity meter extensions can connect to the enclosure 20 in place of or in addition to the extension 40.

Referring now to FIGS. 1A, 1B and 2, schematic representations illustrating various configurations of the dietary intake regulating device 10 configured as the dietary intake and activity meter platform embodiment, in accordance with an embodiment of the present invention, are shown. The dietary intake and activity meter platform embodiment includes the enclosure 20 and the extension 40 that both contain various electrical components. The enclosure 20 is configured to operate either as a stand-alone device (device 203 in FIG. 1B containing a food carrier portion 204, where the food carrier portion 204 is a regular kitchen utensil such as a tablespoon and not an extension 40) or as a main component that connects to detachable (device 201 in FIG. 1B), detached (FIG. 1A and device 202 in FIG. 1B) or permanently attached (device 200 in FIG. 1B) extensions 40. The enclosure 20 can also be configured to operate as a folding multi-function knife by permanently attaching several extensions 40 with a folding mechanism such as, e.g., a Swiss army knife with a spoon, knife, fork, and the like. The enclosure 20 can accept any extension 40 that operates as a dietary intake regulator or meter for pacing bites or measuring calories and fat consumed, and/or an activity meter for measuring physical activities, calories and fat burned or measuring sleeping activities. Suitable extensions 40 include, for example, food carrier extensions 41 such as a utensil food carrier extension 42 and a non-utensil food carrier extension 43, and activity meter extensions 44 such as a pedometer, sleep meter and the like.

Referring again to FIGS. 1A, 1B and 2, schematic representations illustrating various exemplary configurations for operation of the dietary intake regulating device 10 or the dietary intake and activity meter platform embodiment in a dietary intake mode (extensions 41 in FIG. 1A, 42 in FIGS. 1B and 43 in FIG. 2) to primarily detect bites, or for operation of the dietary intake and activity meter platform embodiment in an activity mode (extension 44 in FIG. 1A) to primarily detect activity or non-activity behaviors, are shown. In the dietary intake mode, the enclosure 20 can be either a handle (FIG. 1B), i.e., the part of the dietary intake and activity meter platform embodiment that is touched by the user's hand to carry food, or a casing (FIG. 2) that is attached to the user's hand, wrist, finger, or other body part using rings (not shown), bracelets 23, straps (not shown), clips (not shown), and the like. In the activity mode, the enclosure 20 can be a casing that is kept in user's pocket, bag, purse and the like, or clipped/attached to a necklace, a belt, a cloth garment and the like.

If desired, the enclosure 20 may be configured to be electrically isolated using an electrical isolation material 21 (FIG. 1B) from the extension 40 depending on the sensors that are used in the extension 40.

The enclosure 20 (FIG. 4) may have analog or digital signal links to the extensions 40 (FIG. 5), a remote station 50 (FIGS. 6 and 7), a third party device 60 (FIG. 7) or any desired combination thereof. A processor unit 24 (FIG. 4) receives the sensor signals via direct electrical connections (devices 200 and 201 in FIG. 1B), wireless communication 45 (FIG. 1A, and device 202 in FIG. 1B) or wired communication 146 (FIG. 2).

The external casings of the dietary intake regulating device 10 and the dietary intake and activity meter platform embodiment, that is, the enclosure 20 and the extension 40, can be made of various well-known materials used in the manufacture of electronic devices, such as metals and plastics. The dietary intake regulating device 10 and the enclosure 20 typically include a display casing made of any material (plastic, glass, and the like) that is transparent enough to display data.

Figure 4:
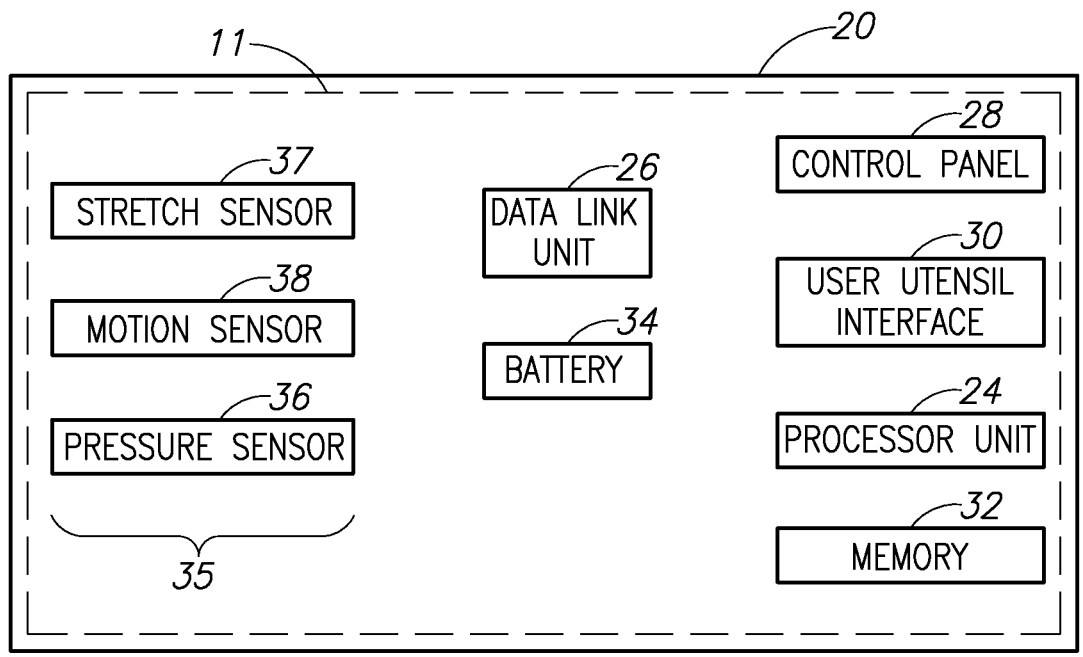
FIG. 4 is a block diagram of an exemplary enclosure, in accordance with the preset invention.

Referring now to FIG. 4, a block diagram representation of an exemplary electric circuit 11 for inclusion in the dietary intake regulating device 10 or an exemplary enclosure 20, in accordance with an embodiment of the present invention, is shown. The electric circuit 11 or the enclosure 20 in the illustrated embodiment include a processor unit 24, a data link unit 26, a control panel 28, a user-utensil interface 30, a memory unit 32 and a battery unit 34. The electric circuit 11 or the enclosure 20 also include a plurality of sensors 35 such as a pressure sensor 36, a stretch sensor 37 and a motion sensor 38. However, it should be understood that components can be added to or removed from the electric circuit 11 or the enclosure 20 or otherwise changed without departing from the scope of the present invention.

The processor unit 24 of the dietary intake regulating device 10 is configured to accurately detect a bite of food by the user, using one or any combination of sensors located in the electric circuits 11. The processor unit 24 of the enclosure 20 is configured to accurately detect a bite, the activity, and the non-activity of the user, using one or any combination of sensors located in the enclosure 20 and the extension 40. The processor unit 24 of the dietary intake regulating device 10 or the enclosure 20 processes the signals and information from input components or devices such as control panels, counters, timers, sensors and the like, stores processed information in the memory unit 32, and delivers processed information and associated alerts to components of the user-utensil interface 30 such as visual, optical, audible, and/or tactile signal devices.

The data link unit 26 is configured to send and receive data or signals to and from the electric circuits 11 (FIGS. 4, 5 and 6), remote stations 50 (FIG. 6), third party devices 60 (FIG. 7) or various combinations thereof. In another embodiment, the data link unit 26 is configured to send and receive data or signals to and from the enclosure 20 (FIG. 4), extensions 40 (FIG. 5), remote stations 50 (FIG. 6), third party devices 60 (FIG. 7) or various combinations thereof. The data links 26 can be based on wired communication, such as PS/2, USB, FireWire, DVI, HDMI, Serial, Parallel, and the like, or on wireless communication, such as IR, RF, Bluetooth, WLAN, WWAN, 3G, and the like, or various combinations of wired and wireless communication. The data links may be enabled manually, such as by plugging in a USB cable, or automatically, such as by connecting automatically when in the proximity of a Bluetooth transmitter. In the case of wireless data links, the data link unit 26 includes an antenna to receive and transmit data or signals.

The control panel 28 is configured to allow the user to control any configurable data or settings, such as display settings, alert types, time between two bites, number of calories associated with bites and the like. The technology of the control panel 28 can contain a button, a switch, a motion sensing action using motion sensors, a touch sensing action using touch sensors, a mechanical timer, and the like. The control panel 28 may allow a user to turn the dietary intake eating device 10 or the dietary intake and activity meter platform embodiment thereof on and off, increase or decrease the number of minutes of the satiety timer or bite timer, switch between visual, audible and tactile signaling device or any combination thereof, and the like. For example, a double-tap on the dietary intake regulating device 10 or the dietary intake and activity meter platform embodiment may change the display settings, or a mechanical timer may be set as a satiety meter to measure the time since the beginning of the meal.

The user-utensil interface 30 is configured to produce visual, optical, audible, and/or tactile signals based on specific events or alerts generated by the processor unit 24 such as bite number, bite time interval, battery level, setting, bite history, and the like. The user-utensil interface 30 can include a visual or optical signaling device that is configured to inform or alert the user based on specific events. The technology of the visual or optical signaling device may use Light-emitting diode (LED), Liquid Crystal Display (LCD), Plasma, Digital Light Processing (DLP), Liquid Crystal on Silicon (LCOS), Direct Drive Image Light Amplifier (D-ILA), Cathode Ray Tube (CRT), High Temperature Poly-Silicon (HTPS), Surface-conduction Electron-emitter Display (SED), electro-luminescent backlight technology and the like. The visual or optical signaling device may use one or more of a numerical display, text display, graphical display, blinking indicator, color indicator, and the like. The user-utensil interface 30 can include an audible signaling device that is configured to calm, alert or inform the user based on specific events. The technology of the audible signaling device can be a miniature speaker or vibrator and the like. The audible signal may be a buzz, music or voice announcing the data or a healthy tip based on the alert type. The user-utensil interface 30 can include a tactile signaling device that is configured to alert the user based on specific events. The technology of the tactile signaling device can be a miniature vibrator, a small heating component, and the like.

The memory unit 32 is configured to record any data generated internally from sensors, timers and other components or to receive data sent by an external device via data links. The memory unit may be split in two areas or sub-units: one only accessible by the processor unit, known as primary storage where the processor unit reads instructions stored there and executes them as required, and a second one not directly accessible by the processor unit, known as secondary storage, that is used to store any type of data such as event logs, music files, video files, personal files, and the like. The technology used for the memory can be a removable or non-removable memory such as flash memory, Random Access Memory (RAM), USB drive, Hard Disk Drive (HDD), Secure Digital (SD), Mini-SD, Micro-SD, and the like. Data may be encrypted based on the need to secure data and protect its access.

The battery unit 34 can be configured to include a removable battery, which can be a rechargeable or a replaceable battery, or a non-removable, rechargeable battery. The battery unit 34 can also be configured as a power supply port which can connect directly to an external power supply source. The battery unit 34 is used to provide power to the dietary intake regulating device 10, the dietary intake and activity meter platform embodiment or the remote station 50.

Figure 5:
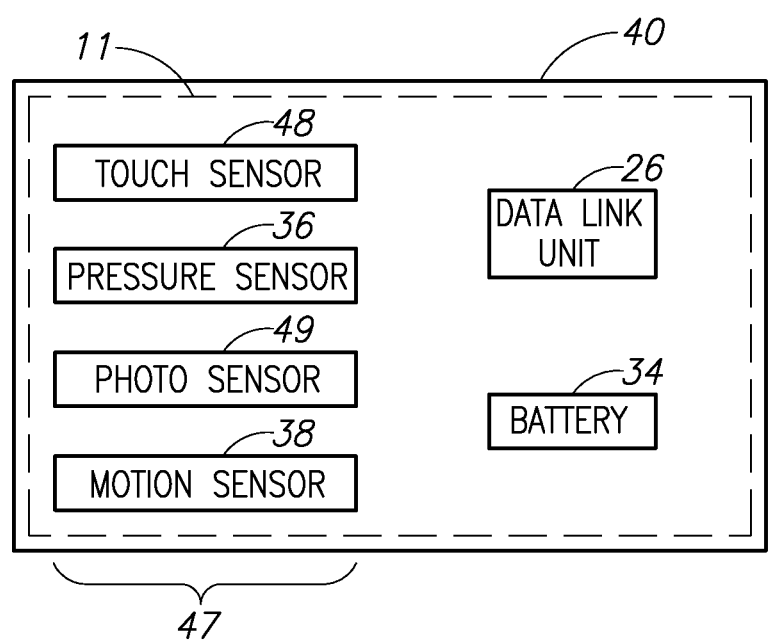
FIG. 5 is a block diagram of an exemplary extension, in accordance with the present invention.

Referring now to FIG. 5, a block diagram of an exemplary extension 40, that includes an exemplary electric circuit 11, in accordance with an embodiment of the present invention, is shown. The extension 40 in the illustrated embodiment includes a set of complementary sensors 47 such as the pressure sensor 36, the motion sensor 38, a touch sensor 48 and a photo sensor 49. In general, the extensions 40 are dietary intake meters, activity meters or non-activity meters. As discussed above, the extensions 40 can be configured to be detached (FIG. 1A and device 202 in FIG. 1B), detachable (device 201 in FIG. 1B) or permanently attached (device 200 in FIG. 1B) to the enclosure 20. Extensions 40 that are detached or detachable can be easily replaced with another extension 40, thereby allowing the use of multiple dietary intake and activity meters with a single enclosure 20. The extension 40 communicates data or sensor signals to the processor unit 24 of the enclosure 20 via direct electrical connections or via data links generated by data link units on both the extension 40 and the enclosure 20.

Figure 7:
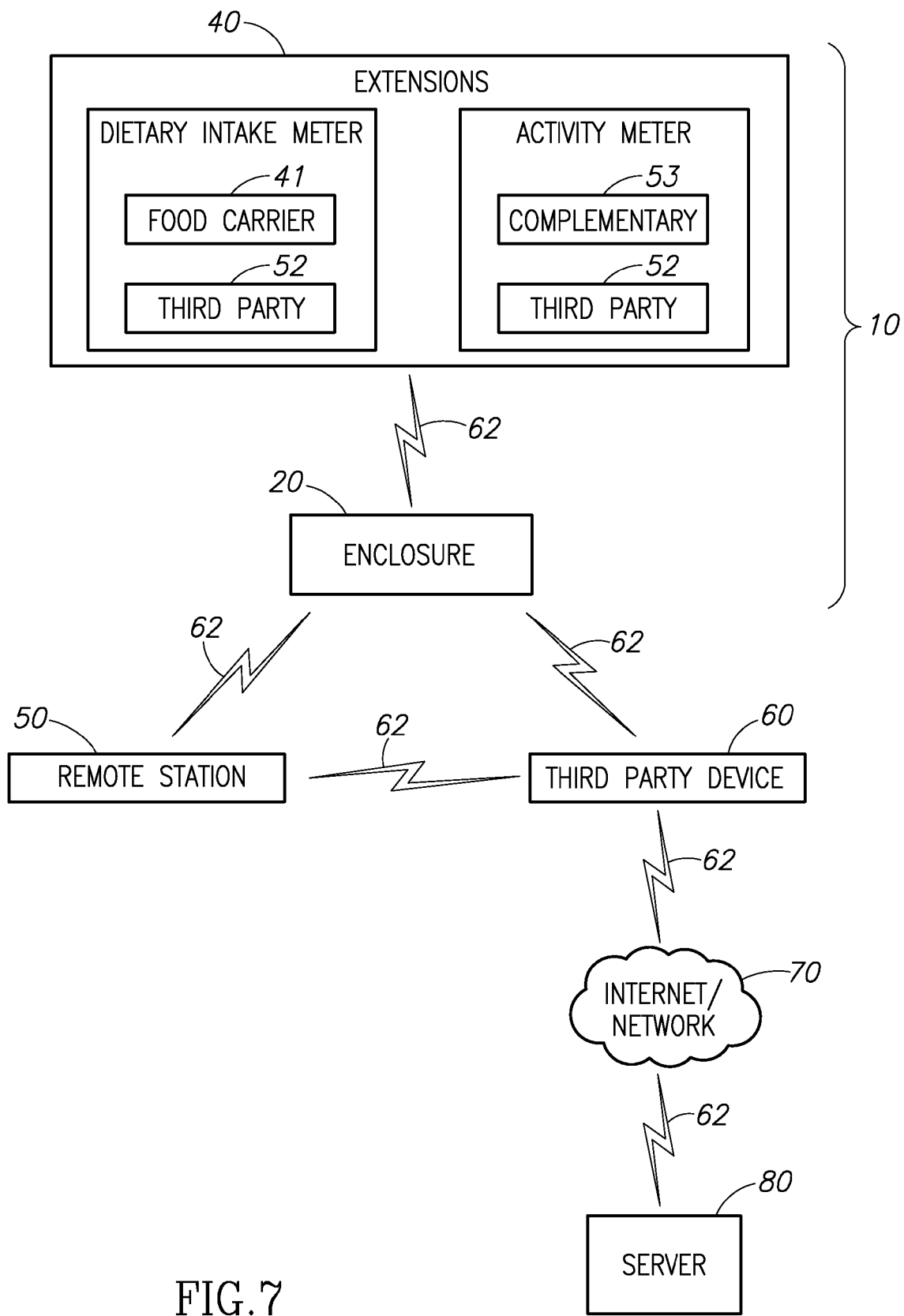
FIG. 7 is a block diagram of an alternate embodiment in which a third party device, Internet or network access and a server are used in conjunction with a remote station and a dietary intake regulating device, in accordance with the present invention.

In general, the extension 40, when used as a dietary intake meter, can be any device that measures dietary intake. Suitable dietary intake meter extension include, for example, food carrier extensions 41 (FIGS. 1A, 1B and 2) and third party extensions 52 (FIG. 7). A food carrier extension 41 is configured to work with the enclosure 20 to detect bites. The food carrier is the part of the food carrier extension 41 that touches and carries food to the mouth, and, in the case of an utensil food carrier extension 42, subsequently touches or enters the mouth partially or entirely. The food carrier may include one or more of the complementary sensors 47, such as the pressure sensor 36, the motion sensor 38, the touch sensor 48, and the photo sensor 49. Signals from the complementary sensors 47 are sent to the processor unit 24 of the enclosure 20 to improve the bite detection accuracy. The food carrier extension 41 can be the utensil food carrier extension 42 or the non-utensil food carrier extension 43. The utensil food carrier extension 42 can be one or more of a fork, a spoon, a chopstick, a knife, or any other similar eating utensil that allows the user to carry food to his or her mouth (FIGS. 1A and 1B). The non-utensil food carrier extension 43 can be a food holder that reduces bare hand food contact such as a finger cap 205 (FIG. 2), a glove, a food wrapper, a food grabber, or any other similar non-utensil food holding device that allows the user to bring food to his or her mouth using bare hands (FIGS. 1A and 2). The third party extension 52 (FIG. 7) is a self-contained device that is configured to measure dietary intake of a food substance such a liquid or solid food, a beverage, and the like. The third party extension 52 may be a chewing system that measures the number of times food is chewed, a manual bite counter, and the like. The third party extension 52 processes internally the sensor signals and sends final processed results or data events to the processor unit 24 of the enclosure 20.

In general, the activity meter extension 44 can be any device that measures human physical activity or resting periods, such as a pedometer, a sleep meter, a physical apparel activity meter, a swimming distance meter, and any similar activity or non-activity meter device. The activity meter extension 44 has two benefits. First, the enclosure 20 may have a limited set of sensors due to the small enclosure size and volume. Therefore the measurement accuracy can be increased by adding a similar or different set of sensors in the activity meter extension 44, such as a heart beat sensor, a sweat sensor, and the like. Second, the measurement accuracy can be improved by adding redundancy to the system and decentralizing the sensors at different locations, for example, the enclosure 20 in the hand and the activity meter extension 44 clipped on cloth. Suitable activity meter extensions 44 include, for example, complementary extensions 53 and the third party extensions 52 (FIG. 7). A complementary extension 53 is configured to work with the enclosure 20 to detect and measure a user's activity or non-activity levels, sleep behaviors, and the like. The activity meter extension 44 in this instance contains one or more of the complementary sensors 47 for this purpose. Signals from the complementary sensor 47 are sent to the processor unit 24 of the enclosure 20 to improve the accuracy of activity or non-activity measurements. The third party extension 52 is a self-contained device that processes internally the sensor signals and sends final processed results or data events to the processor unit 24 of the enclosure 20.

Figure 6:
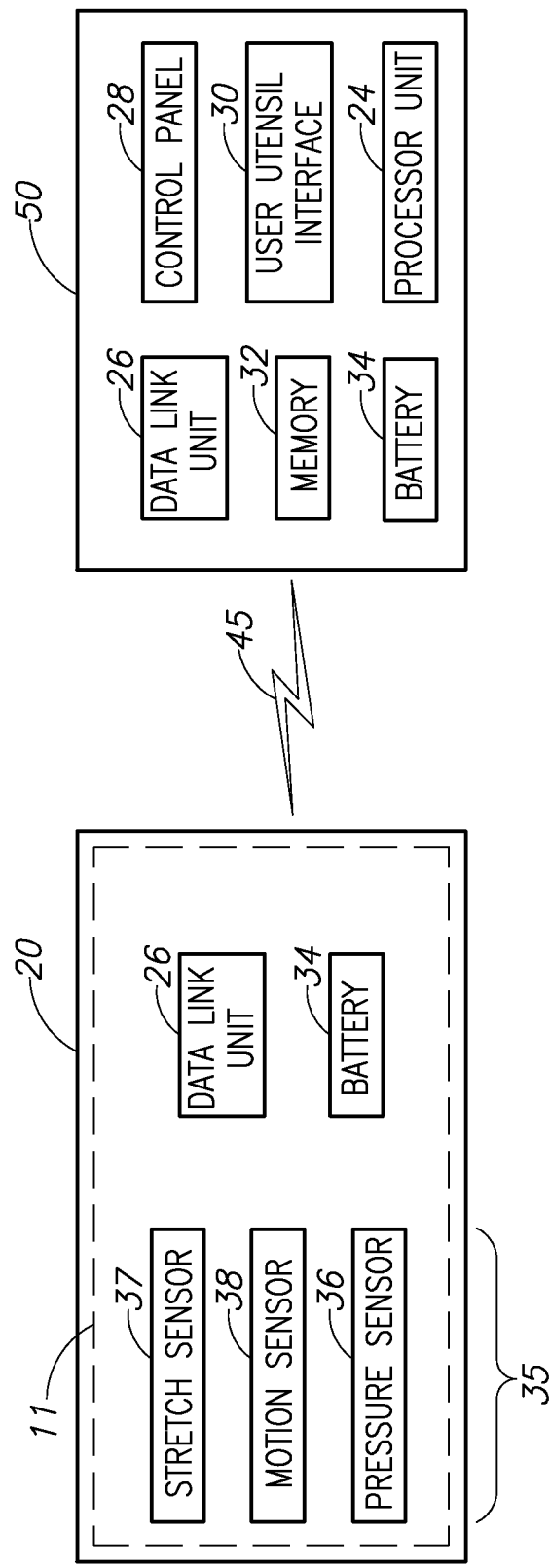
FIG. 6 is a block diagram of an exemplary remote station communicating with an exemplary enclosure, in accordance with the present invention.

In alternate embodiments of the present invention, a remote station 50 can be used with the dietary intake regulating device 10 or the dietary intake and activity meter platform embodiment of the present invention. The remote station 50 is configured to control and monitor the dietary intake regulating device 10 or the dietary intake and activity meter platform embodiment configurable data, settings, specific events, alerts, and the like. A block diagram of an exemplary remote station 50, in accordance with an embodiment of the present invention, is shown in FIG. 6, which depicts a specific case where some components of the electric circuit 11 or the enclosure 20, that is, a memory unit 32, a control panel 28, a user-utensil interface 30, or a processor unit 24, are located only in the remote station to save power and space. The remote station 50 is configured to communicate via data links with either or both the dietary intake regulating device 10 or the dietary intake and activity meter platform embodiment and third party devices 60 (FIG. 7), and to alert the user of any event, statistic, and the like. The remote station 50 is either a standalone replica of the dietary intake regulating device 10 or the enclosure 20 without sensors 35 or an external device such as a PDA, a Smartphone, a laptop computer, a desktop computer, a game console, an access point and the like. One or more of the control panel 28, the human-utensil interface 30, the memory unit 32, the data link unit 26, the battery unit 34, and the processor unit 24 may be duplicated or emulated on the remote station 50 or simply located on the remote station 50 instead of the dietary intake regulating device 10 or the dietary intake and activity meter platform embodiment. Based on the sensor data/signals received from the dietary intake regulating device 10 or the dietary intake and activity meter platform embodiment, the remote station 50 can generate the same outputs, alerts, statistics, and the like, as the dietary intake regulating device 10 or the dietary intake and activity meter platform embodiment. The remote station 50 may be used as a stand-alone meal duration timer, aka satiety meter, with its own meal duration target which is set manually by the user or automatically when first bite detected. Functions which can be included in the remote station 50 include, for example, one or more of the following: the remote station 50 can allow the user to remotely modify configurable data or settings on the dietary intake regulating device 10 or the dietary intake and activity meter platform embodiment; the remote station 50 can allow the user to remotely visualize any available data, receive vibration alerts or hear an audio message based on alerts, where data or alerts are generated by the dietary intake regulating device 10 or the dietary intake and activity meter platform embodiment; the remote station 50 can receive all the sensor data from the dietary intake regulating device 10 or the dietary intake and activity meter platform embodiment and operate as the processor unit 24 of the dietary intake regulating device 10 or the enclosure 20 in order to compute statistics or events; and the remote station 50 can be a game console that displays an electronic game where the dietary intake regulating device 10 or the dietary intake and activity meter platform embodiment are configured to control an appearance such as actions or movements of a game character on the display screen and therefore can show the character taking bites when bites are detected by processor unit 24, or show the character going from a plate to the mouth or from the mouth to the plate, or the like.

Referring now to FIG. 7, a block diagram of an alternate embodiment of the present invention is shown in which a third party device 60, Internet/network access 70 and a server 80, such as a website server, application server and the like, are used in conjunction with the remote station 50 and the dietary intake regulating device 10 or the dietary intake and activity meter platform embodiment. In the illustrated embodiment, multiple data links 62 are used to provide connectivity between and among the various illustrated components. Third party devices 60 are configured to provide connectivity and access to a server 80, in which case suitable third party devices 60 include, for example, modems, routers, access points, PDA's, Smartphones, laptop computers, desktop computers, game consoles and the like. The third party device 60 can also be configured to run a software in relation to the dietary intake regulating device 10 or the dietary intake and activity meter platform embodiment, such as a calorie balance software, a dietary management software and the like, in which case suitable third party devices 60 include, for example, PDA's, Smartphone, laptop computers, desktop computers, game consoles and the like. The third party device 60 can connect to the Internet or a network 70 to store or retrieve information (such as dietary intake regulating device 10 data, the dietary intake and activity meter platform embodiment data, calorie events, and the like) on the server 80. One or both of the dietary intake regulating device 10 or the enclosure 20 and the remote station 50 connect and communicate via data links 62 with the third party device 60 to synchronize their data, i.e., store/retrieve information (such as dietary intake regulating device 10 data, the dietary intake and activity meter platform embodiment data, calorie events, and the like), on the server 80 or third party device 60 software. When connected, the dietary intake regulating device 10 or the enclosure 20 and the remote station 50 synchronize manually or automatically their data with the data on the user's account of the third party device 60 software or server 80. Simultaneously the dietary intake regulating device 10 or the enclosure 20 and the remote station 50 can also send their data to a third party account of the third party device 60 software or server 80, such as an account of the personal coach, nutritionist, health primary physician, insurance company, and the like, to evaluate the user data; in this case data may be encrypted for security and privacy reasons and, if desired, to prevent users from falsifying the data.

The server 80 and the third party device 60 software are configured to allow the dietary intake regulating device 10 and the dietary intake and activity meter platform embodiment users to record any data related to dietary intake, physical activity, non-activity, sleep behavior, calories and the like. In addition to recording and managing all data from the dietary intake regulating device 10, enclosure 20 or the remote station 50, the third party device 60 software and server 80 can receive, record, and track any activity from any device that counts the number of calories consumed and/or burned. The server 80 or the third party device 60 software may or may not be specifically dedicated to the dietary intake regulating device 10 or the dietary intake and activity meter platform embodiment.

As noted above, the dietary intake regulating device 10 of the present invention contains one more sensors located in the electric circuits 11. The sensors are configured alone or in combination to detect a user's bite. Various types of sensors can be used, including without limitation pressure sensors 36, stretch sensors 37, motion sensors 38 such as single-/multi-axis angular or linear motion sensors, touch sensors 48 and photo sensors 49 (See, FIGS. 1B, 2, 3, 4 and 5).

As noted above, the dietary intake and activity meter platform embodiment of the present invention contains one more sensors located in the enclosure 20 and the extension 40. The sensors are configured alone or in combination to detect a user's bite, an activity or a non-activity. Various types of sensors can be used, including without limitation pressure sensors 36, stretch sensors 37, motion sensors 38 such as single-/multi-axis angular or linear motion sensors, touch sensors 48 and photo sensors 49 (See, FIGS. 1B, 2, 3, 4 and 5).

Figure 3:
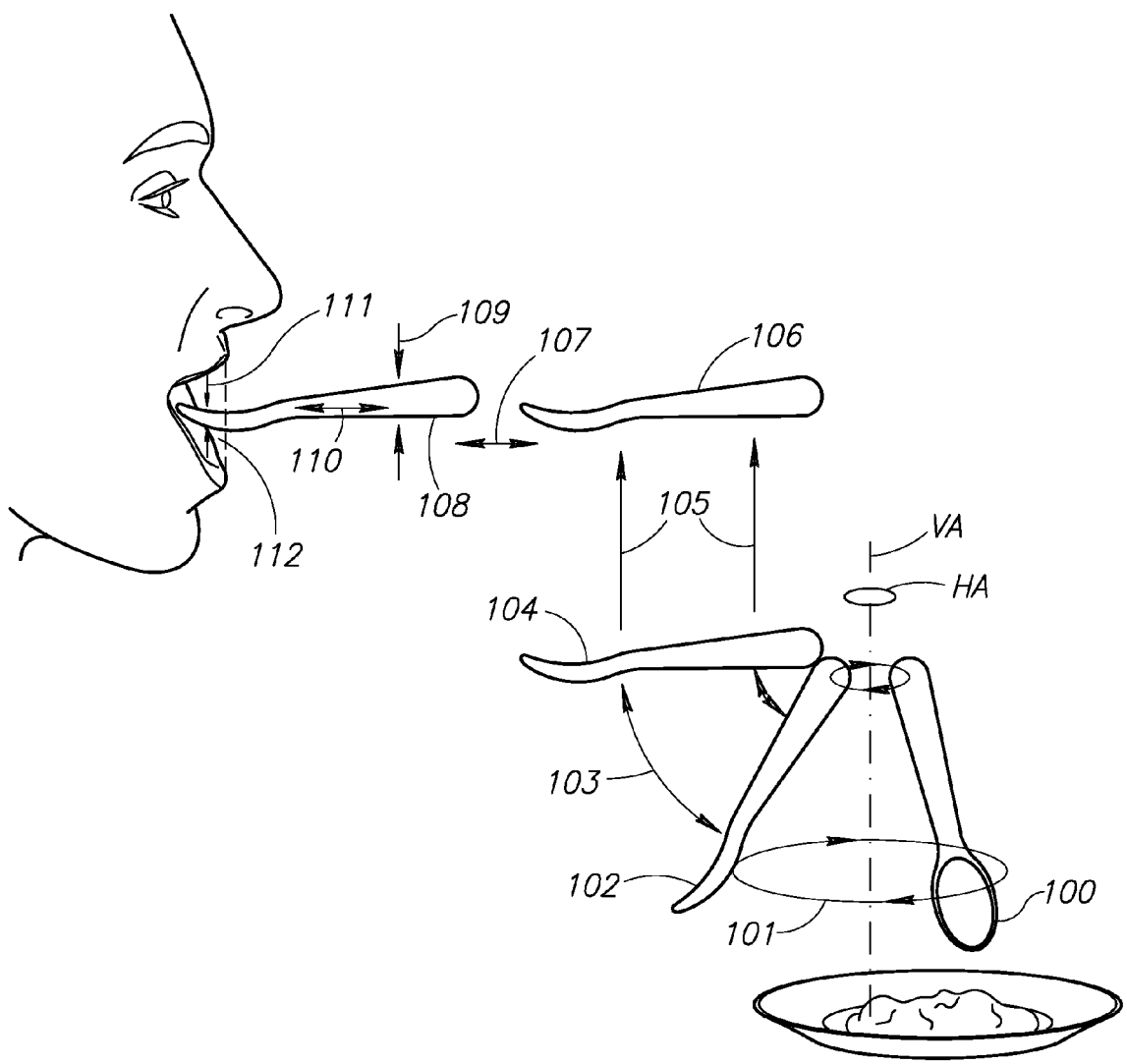
FIG. 3 is a schematic representation illustrating one exemplary method of measuring bites of food taken by a user, in accordance with the present invention.

The pressure sensor 36 (FIGS. 1B, 2, 3, 4 and 5) is configured to sense the pressure 109/120 variations of the fingers or hand on either the dietary intake regulating device 10, the enclosure 20 or the non-utensil food carrier 43 created when a bite of food is taken like in exemplary position 108 of FIG. 3 and the hand starts leaving the proximity of the mouth such as in exemplary position 106 of FIG. 3. The pressure sensor 36 (FIG. 3) is also configured to sense the pressure 111 of the mouth or teeth on the dietary intake regulating device 10 food carrier portion or the utensil food carrier extension 42 when a bite is taken. The pressure sensor 36 is also configured to sense the pressure created by the food weight on the dietary intake regulating device 10 food carrier portion or the utensil food carrier extension 42 prior to the user's bite to automatically regulate the bite duration target, to adjust the amount of calories assigned to each bite or both. The pressure sensor 36 may be based on sensing technologies including but not limited to capacitive sensing, resistive sensing, surface acoustic wave sensing, touch sensing, optical sensing, piezoelectric sensing, piezocapacitive sensing, piezoresistive sensing, inductive sensing, electromechanical sensing, mechanical sensing, potentiometric sensing, strain gauge sensing, and the like. Furthermore, the pressure sensing mechanism may be based on single point sensing (using a single pressure sensor) or multipoint sensing (using multiple pressure sensors). Single point sensing is capable of only distinguishing a single pressure, while multipoint sensing is capable of distinguishing multiple pressures that occur at the same time. The pressure sensor 36 can be located on the food carrier portion of the dietary intake regulating device 10, the enclosure 20 or the food carrier extension 41.

The touch sensor 48 (FIGS. 1B, 3 and 5) is configured to sense the touch 111 of the mouth or teeth with the tip of dietary intake regulating device 10 food carrier portion or the utensil food carrier extension 42 in the case of single point sensing, to sense the succession of touches 111 of the mouth or teeth created by the removal of the food carrier portion of the dietary intake regulating device 10 or the utensil food carrier extension 42 from the proximity of the mouth after a bite in the case of multi point sensing, or both. The touch sensor may be based on sensing technologies including but not limited to capacitive sensing, resistive sensing, surface acoustic wave sensing, pressure sensing, optical sensing, piezoelectric sensing, piezocapacitive sensing, piezoresistive sensing, inductive sensing, electromechanical sensing, mechanical sensing, potentiometric sensing, strain gauge sensing, and/or the like. Furthermore, the touch sensing mechanism may be based on single point sensing (using a single touch sensor) or multipoint sensing (using multiple touch sensors). Single point sensing is capable of only distinguishing a single touch, while multipoint sensing is capable of distinguishing multiple touches that occur at the same time. The touch sensing device is located on the food carrier portion of the dietary intake regulating device 10 or the utensil food carrier extension 42.

The stretch sensor 37 (FIGS. 1B, 3, 4 and 6) is configured to sense the stretch 110 between the food carrier portion and the non-food carrier portion of the dietary intake regulating device 10 when a bite is taken and the dietary intake regulating device 10 is simultaneously removed from the mouth or between the enclosure 20 and the utensil food carrier extension 42 when a bite is taken and the dietary intake and activity meter platform embodiment is simultaneously removed from the mouth. The stretch sensor 37 may be based on sensing technologies including but not limited to capacitive sensing, resistive sensing, surface acoustic wave sensing, pressure sensing, touch sensing, optical sensing, piezoelectric sensing, piezocapacitive sensing, piezoresistive sensing, inductive sensing, electromechanical sensing, mechanical sensing, potentiometric sensing, strain gauge sensing, and the like. Furthermore, the stretch sensing mechanism may be based on single point sensing (using a single stretch sensor) or multipoint sensing (using multiple stretch sensors). Single point sensing is capable of only distinguishing a single stretch, while multipoint sensing is capable of distinguishing multiple stretches that occur at the same time. The stretch sensor 37 is located on the non-food carrier portion of the dietary intake regulating device 10 at the junction between the food carrier portion and the non-food carrier portion or on the enclosure 20 at the junction between the enclosure 20 and the utensil food carrier extension 42.

The photo sensor 49 (FIGS. 1B, 3 and 5) is configured to sense the light intensity 112 variations on the food carrier portion of the dietary intake regulating device 10 or on the utensil food carrier extension 42 when entering and leaving the mouth. The photo sensor 49 may be based on sensing technologies including but not limited to photodiode sensing (operating in photovoltaic or photoconductive modes), phototransistor sensing, photoresistor sensing (aka Light Dependent Resistor), photovoltaic cell (aka solar cell) sensing, photomultiplier tube sensing, phototube sensing, charge-coupled device (CCD) sensing, chemical sensing (e.g., photographic plates), infrared sensing, CMOS sensing, optical sensing, LEDs sensing (reverse biased LEDs to act as photodiodes), and the like. Furthermore, the photo sensing mechanism may be based on single point sensing (using a single photo sensor) or multipoint sensing (using multiple photo sensors). Single point sensing is capable of only distinguishing a single light intensity variation, while multipoint sensing is capable of distinguishing multiple light intensity variations that occur at the same time. The photo sensor 49 is located on the dietary intake regulating device 10 food carrier portion or on the utensil food carrier extension 42. Multipoint sensing provides more accuracy, for example, in another embodiment, by first placing photo sensors on both the enclosure 20 and the utensil food carrier extension 42 and, second, comparing the luminosity difference between the sensors on utensil food carrier extension 42 and the enclosure 20, and therefore removing any sensor reading errors due to luminosity interferences that can occur during a meal such as opening or closing lights or windows.

The motion sensor 38 (FIGS. 1B, 3, 4, 5 and 6) can be configured to detect the linear physical motion of the dietary intake regulating device 10 or the dietary intake and activity meter platform embodiment between the food receptacle and the mouth by sensing either or both the vertical linear move 105 and the horizontal linear move 107. The motion sensor 38 can also be configured to detect the angular physical motion of the dietary intake regulating device 10 or the dietary intake and activity meter platform embodiment between the food receptacle and the mouth by sensing either or both the vertical angular move 103 and the horizontal angular move 101.

The motion sensor 38 of the dietary intake and activity meter platform embodiment can also be configured to sense the activity of the user based on body movements. The motion sensor 38 detects repetitive motions, such as, the steps that the user makes during a walking or running motion, the stroke when rowing and the forward/upward motion when going up the stairs, and the like, to provide an output indicative thereof. The motion sensor 38 is also configured to sense the non-activity of the user based on body movements. The motion sensor 38 detects periods of no motion with potentially feeble and disparate motions to measure and record daily resting, napping or sleeping intervals. The motion sensor 38 may be based on sensing technologies including but not limited to accelerometer, gyroscope, compass, functional sensors, spring sensing, lever arm sensing, contact sensing, GPS sensing, capacitive sensing, resistive sensing, surface acoustic wave sensing, pressure sensing, touch sensing, optical sensing, piezoelectric sensing, piezocapacitive sensing, piezoresistive sensing, inductive sensing, electromechanical sensing, mechanical sensing, potentiometric sensing, strain gauge sensing, servo devices, CMOS, MEMS and the like. Furthermore, the motion sensing mechanism may be based on single point sensing (using a single motion sensor) or multipoint sensing (using multiple motion sensors). Single point sensing is capable of only distinguishing a single motion, while multipoint sensing is capable of distinguishing multiple motions that occur at the same time, e.g., linear and angular motions. Furthermore, the motion sensing mechanism may be based on single-axis sensing or multi-axis sensing. Single-axis sensing is capable of only distinguishing a motion on a single axis, while multi-axis sensing is capable of distinguishing a motion on multiple axes. The motion sensor 38 is located in the dietary intake regulating device 10, the enclosure 20 or the extension 40.

As noted above, the processor unit 24 of the dietary intake regulating device 10 is configured to accurately detect a bite using one or any combination of the sensors located in the electric circuits 11 (See, FIGS. 1B, 2, 4, and 5).

As noted above, the processor unit 24 of the enclosure 20 is configured to accurately detect a bite, the activity of the user, and the non-activity of the user, using one or any combination of the sensors located in the enclosure 20 and the extension 40 (See, FIGS. 1B, 2, 4, and 5).

Referring now to FIGS. 1B, 2 and 3, bite detection is made possible by combining outputs from several sensors. Bite detection can be determined using the following steps, which typically take place within seconds: (1) depending on the sensors in use and if the processor unit 24 detects that the dietary intake regulating device 10 or the dietary intake and activity meter platform embodiment are below the pre-defined linear and angular thresholds defined in Step 2, one or more of the following occurs, indicating that the user takes food using the dietary intake regulating device 10 or the dietary intake and activity meter platform embodiment,—(a) the touch sensor 48 detects the transition between first the absence of touch when the dietary intake regulating device 10 food carrier portion or the utensil food carrier extension 42 is outside the mouth with no food on it, and second the contact 111 of the dietary intake regulating device 10 food carrier portion the utensil food carrier extension 42 with the food, (b) the pressure sensor 36 detects the transition between first the absence of pressure 111 when the dietary intake regulating device 10 food carrier portion or the food carrier extension 41 is outside the mouth with no food on it, and second the presence of pressure once the dietary intake regulating device 10 food carrier portion or the food carrier extension 41 carries food, (c) the photo sensor 49 detects the transition between first the intense luminosity on the tip of the dietary intake regulating device 10 food carrier portion or the utensil food carrier extension 42 tip when no food or obstacle are present, and second the reduced luminosity created by the food on the dietary intake regulating device 10 food carrier portion or the utensil food carrier extension 42; (2) based on the motion sensor 38 data, the processor unit 24 detects a vertical-up linear motion 105 above a pre-defined linear threshold, typically around 6 inches or its velocity equivalence, and/or a vertical-up angular motion 103 above a pre-defined angular threshold, typically around 45 degrees or its velocity equivalence, of the dietary intake regulating device 10 or the dietary intake and activity meter platform embodiment which indicate that the user starts bringing food from the food receptacle to his or her mouth; (3) the processor unit 24 starts recording all the movements detected by the motion sensor 38, that is, the vertical linear motion 105 and/or horizontal linear motion 107 and/or vertical angular motion 103 and/or horizontal angular motion 101. This set of recorded movements is called "forward sequence" for future reference; (4) depending on the sensors in use, one or more of the following occurs, indicating that the user receives the food in his or her mouth and takes a bite of the food, see exemplary position 108,—(a) the touch sensor 48 detects the transition between first the contact 111 of the food carrier portion of the dietary intake regulating device 10 or the utensil food carrier extension 42 with the food or mouth, for example, jaw, lips, teeth, or tongue, and second the absence of touch 111 when the utensil food carrier extension 42 or the food carrier portion of the dietary intake regulating device 10 leaves the proximity of the mouth, (b) the pressure sensor 36 detects the transition between first the increased pressure 111 of the mouth on the dietary intake regulating device 10 food carrier portion or the utensil food carrier extension 42 while biting and simultaneously removing food from mouth, and second the reduced pressure once the dietary intake regulating device 10 or the dietary intake and activity meter platform embodiment leaves the proximity of the mouth, (c) the pressure sensor 36 detects the transition between first the increased pressure 109/120 of the hand or fingers on the food or non-food carrier portion of the dietary intake regulating device 10, the enclosure 20 or the non-utensil food carrier 43 while biting and simultaneously removing food from mouth, and second the reduced pressure once the dietary intake regulating device 10 or the dietary intake and activity meter platform embodiment leaves the proximity of the mouth, (d) the photo sensor 49 detects the transition between first the reduced luminosity 112 on the tip of the dietary intake regulating device 10 food carrier portion or the utensil food carrier extension 42 tip when the food is in the mouth, and second the more intense luminosity when the dietary intake regulating device 10 food carrier portion or the utensil food carrier extension 42 leave the proximity of the mouth, (e) the stretch sensor 37 detects the transition between first the stretch 10 that occurs on the dietary intake regulating device 10 between the food and the non-food carrier portions or on the dietary intake and activity meter platform embodiment between the enclosure 20 and the utensil food carrier extension 42 while biting and simultaneously removing the dietary intake regulating device 10 or the dietary intake and activity meter platform embodiment from the mouth, and second the absence of stretch when the dietary intake regulating device 10 or the dietary intake and activity meter platform embodiment are outside of mouth; (5) based on motion sensor 38 data, the processor unit 24 stops the recording of motions which was initially started at Step 3, stores the forward sequence data in memory unit 32, starts again recording all movements as in Step 2, and detects a backward sequence oppositely matching the forward sequence by at least a pre-defined percentage, typically 50%; and (6) the bite is officially detected and recorded in the memory unit 32 as such, and the bite detection process restarts at Step 1. Also shown in FIG. 3 for illustration purposes are position locations 100, 102, 104, 106 and 108 of the dietary intake regulating device 10 during the bite detection process.

Alternatively, bite detection is also possible, though less accurate, by going through the following shorter sequences: Steps 1/6, Steps 2/6, Steps 3/5/6, Steps 4/6, Steps 1/2/6, Steps 1/3/5/6, Steps 1/4/6, Steps 1/2/3/5/6, Steps 1/2/4/6, Steps 1/3/4/5/6, Steps 2/3/5/6, Steps 2/4/6, Steps 2/3/4/5/6, Steps 3/4/5/6. If Step 1 is not included in one of the foregoing shorter sequences, then the bite detection process restarts at the first step of the shorter sequence instead of Step 1. If the recorded movement goes below the Step 2 pre-defined thresholds before reaching Step 4 of the bite detection process then, if applicable, the bite detection process restarts at Step 2 and the processor unit 24 stops recording motions which were initially started at Step 2. If the recorded movement goes below the Step 2 pre-defined thresholds at any point in time while at Step 3 then the processor unit 24 stops recording and the bite detection process restarts at Step 2. If Steps 3 and 5 are included in one of the shorter sequences while Step 4 is not included, then Step 5 becomes as follows: based on motion sensor 38 data, the processor unit 24 detects a backward sequence of movements oppositely matching the forward sequence by at least a pre-defined percentage, typically 50%. The processor unit 24 detects accurately the pre-defined thresholds mentioned at Step 1 and defined at Step 2 by automatically resetting and recording the vertical reference level of the food receptacle each time the dietary intake regulating device 10 or the dietary intake and activity meter platform embodiment are kept immobile more than a pre-defined time, typically 15 seconds, which occurs when the user rests the dietary intake regulating device 10 or the dietary intake and activity meter platform embodiment at the food vertical level, for example on the food receptacle; for accuracy this process should occur at least one time per meal, typically when powering on the dietary intake regulating device 10.

Activity detection occurs when an activity is sensed by the motion sensors 38 of the dietary intake and activity meter platform embodiment. The activity is then classified as a step motion or as a non-step motion. If an activity is detected as a step motion at a low rate, then the motion is categorized as walking and if at a high rate, then the motion is categorized as running. If an activity is detected but not as a step motion, the activity is classified as non-step motion. If an activity is detected as non-step motion for a duration of less than a threshold, typically two minutes, then the motion is categorized as effort and if for a duration of more than the threshold, then the motion is categorized as a workout. Each walking/running/effort/workout categories are recorded separately and may correspond to different levels of negative calorie assignments.

Non-activity detection occurs when no or little activity is sensed by the motion sensors 38 of the dietary intake and activity meter platform embodiment. If the period of non-activity lasts for more than a low threshold, typically 5 minutes, it is categorized as rest, for more than a medium threshold, typically 15 minutes, it is categorized as a nap and for more than a high threshold, typically 60 minutes, it is categorized as sleep. Each rest/nap/sleep categories are recorded separately and may correspond to different levels of negative or positive calorie assignments.

The processor unit 24 of the dietary intake regulating device 10 or the enclosure 20, in addition to being configured to accurately detect a bite (in the case of the dietary intake regulating device 10 and the dietary intake and activity meter platform embodiment), the activity of the user, and the non-activity of the user (in the case of the dietary intake and activity meter platform embodiment), can also be configured to perform various other functions and to detect or calculate various other parameters, including without limitation functions and parameters such as a bite counter, a bite duration timer, a meal duration timer, a meal interval timer, a caloric value, a caloric data calculator, a bite duration target, a meal duration target and a caloric balance score.

The bite duration target is a pre-defined value set by the user or automatically generated based on user characteristics. The bite duration target corresponds to the minimum recommended chewing duration after a bite is taken in order to properly chew food prior to ingurgitate. The recommended bite duration target is typically about 18 seconds. The pressure sensor 36 on the food carrier portion of the dietary intake regulating device 10 or the food carrier extension 41 can be used to sense the weight of the food on the food carrier prior to the bite detection to augment/reduce proportionally the bite duration target when heavy/light food is sensed.

The bite counter is configured to keep track of the number of bites during a meal. Each bite taken is converted into calories based on either or both the user's input and food weight.

The bite duration timer is configured to keep track of the duration between two bites and to verify if the time interval between two bites is smaller or greater than the bite duration target. The bite duration timer and the bite counter are computed as follows: (a) the bite counter is reset when the first bite of the meal is detected; (b) the bite counter is incremented, the bite duration timer is reset and then starts and the date and time of the new bite is recorded; (c) the relevant eating statistics are signaled to the user such as the bite counter value, the bite duration timer, the remaining time before bite duration target and the like; (d) an alert is triggered if the bite duration timer is greater than the bite duration target; (e) a new bite is detected; (f) the bite duration timer is stopped and the duration of the previous bite is recorded in memory; and (g) the process restarts at step (b) unless the end of the meal is detected which stops the bite duration timer.

The meal duration target is a value defined by the user or automatically generated based on user characteristics, such as body weight, body height, and the like. The meal duration target corresponds ideally to the minimum recommended length of a meal in order to feel satiety. The recommended meal duration target is typically about 20 minutes.

The meal duration timer is configured to keep track of the duration of the meal and to verify if the meal length was greater or less than the meal duration target. The first bite of the meal is detected when a bite is detected while the meal duration timer is stopped. The meal duration timer is initialized and started when the device or platform detects the first bite of the meal. The meal duration is displayed as either or both the time elapsed of the meal since the first bite and the remaining time before reaching the meal duration target. The end of the meal is detected after no bite occurs for more than a designated number of minutes (typically 10 minutes), when the user manually turns the device or platform off, or when the device or platform automatically shuts-off. Once the end of the meal is detected, the meal duration timer is stopped and the time elapsed between the last detected bite and the end of the meal is removed from the meal duration timer. Therefore, the meal duration corresponds to the duration between the first detected bite and the last detected bite of the meal. The date and time of the meal corresponds to the date and time of the first bite of the meal. The date, time and duration of the meal is stored in the memory unit 32, and the dietary intake regulating 10 device or the dietary intake and activity meter platform embodiment may now shut-off if manually or automatically requested in the foregoing steps.

The meal interval timer is configured to keep track of the time elapsed since the end of the last recorded meal. One pre-defined "low" threshold, typically 3 hours, is set to differentiate between the categories "Not allowed to eat" and "Eat at anytime". Another pre-defined "high" threshold, typically 5 hours, is set to alert the user when he or she enters the "Urgent to eat now" category. At any time the user can turn on the dietary intake regulating device 10, the dietary intake and activity meter platform embodiment or the remote station 50 and verify the time elapsed and the category type. Therefore, when the user turns the device, platform, or remote station on, he or she can automatically visualize if it is too early or time to eat. Furthermore automatic alerts are generated based on user's pre-defined goals and can optionally turn on the device, the platform, or the remote station to signal to the user when too much time has elapsed since the end of the last meal, when a user's pre-defined goal is reached or when entering the "Urgent to eat now" category.

The caloric value is computed by the processor unit 24 based on information from the user, the dietary intake regulating device 10, the dietary intake and activity meter platform embodiment, the remote station 50 and, if desired, third party devices 60, or any combination of the foregoing devices. The caloric value is stored in the caloric data.

The caloric data calculator is configured to compute the caloric data. The caloric data is created for each detected event from which calories burned or gained can be estimated. The caloric data contains the date and time stamps for the event, any information that can later be converted into a caloric value, such as the number of steps, the number of bites, the quantity and type of food or liquid, the duration and type of an activity (e.g., swimming duration, and the like), a positive or negative caloric value, such as, "+50" calories, "−120" calories, and the like, or any combination of the foregoing information. The caloric data is first generated by the dietary intake regulating device 10, the dietary intake and activity meter platform embodiment, the remote station 50 or third party devices 60, such as a pedometer, a PDA, a Smartphone, a laptop computer, and the like. The third party devices 60 connect manually or automatically to the dietary intake regulating device 10, the dietary intake and activity meter platform embodiment, or the remote station 50 via data links. The third party devices 60 send the caloric data to the dietary intake regulating device 10, the dietary intake and activity meter platform embodiment or the remote station 50. The processor unit 24 computes the caloric value, if not already present in the caloric data, based on the information contained in the caloric data. The caloric value is integrated in the caloric data. The newly processed caloric data is stored in the memory unit 32.

The calorie balance score is configured to track on-the-fly the calorie balance and the calories in/out of the user. The calorie balance score is displayed and constantly updated on the user-utensil interface 30. The calorie balance score may be displayed as a daily, weekly, monthly or yearly score or the like, as desired. The calorie balance score is obtained by processing the caloric data of the dietary intake regulating device 10, the dietary intake and activity meter platform embodiment (enclosure 20 and/or the extension 40), the remote station 50, and/or third party devices 60. The calorie balance score is computed by the processor unit 24 of the dietary intake regulating device 10, the dietary intake and activity meter platform embodiment or the remote station 50 and updated as soon as a new caloric data is stored in the memory unit 32. The dietary intake regulating device 10, the dietary intake and activity meter platform embodiment or the remote station 50 alert the user based on user's pre-defined calorie balance score goals, e.g., when the calorie balance score goes from positive to negative or negative to positive, to stop eating during a meal to reduce calorie intake, or to increase the current physical activity to burn more calories.

If desired, the dietary intake regulating device 10 or the dietary intake and activity meter platform embodiment of the present invention can incorporate other functions or features in addition to those discussed above, including without limitation a music player, an FM/AM radio, a video player, a clock, an alarm clock, a count-up or count-down timer and the like.

The music player can be controlled manually by the user or automatically based on alert types. The dietary intake regulating device 10 or the dietary intake and activity meter platform embodiment may play sound tracks with relaxing music, subliminal or audible messages during the meal and adapt the music or messages based on generated alerts to develop healthy eating (in the case of device 10 and the platform embodiment) and sports (in the case of the platform embodiment) habits. The dietary intake regulating device 10 or the dietary intake and activity meter platform embodiment may decode any type of audio format such as WAV, MP3, OGG, WMA, and the like.

The FM/AM radio and the video player can be controlled manually by the user or automatically based on alert types. The dietary intake regulating device 10 or the dietary intake and activity meter platform embodiment may play any type of video, such as movies, music videos, and the like with or without subliminal pictures to help the user maintaining good eating (in the case of device 10 and platform embodiment) or sports (in the case of platform embodiment) habits. The device or platform may adapt the video or messages based on generated alerts. The dietary intake regulating device 10 or the dietary intake and activity meter platform embodiment may decode any type of video format such as DivX, MPEG, SWF, MOV, MP4, AVI, DVD, VCD, and the like.

The dietary intake regulating device 10 or the dietary intake and activity meter platform embodiment of the present invention can also incorporate: the clock with multiple clocks & time zones and a calendar, to tag all events, such as bites (in the case of device 10 and platform embodiment) or steps (in the case of platform embodiment), with time and date stamps; the alarm clock to alert the user of specific events, such as meal, snack, or sport time; and the count-up or countdown timer to count to/from a target date and time with alarm.

It should be understood that the present disclosure is not limited to the embodiments disclosed herein as such embodiments may vary somewhat. It is also to be understood that the terminology employed herein is used for the purpose of describing particular embodiments only and is not intended to be limiting in scope and that limitations are only provided by the appended claims and equivalents thereof.

The embodiments of the invention in which an exclusive property or privilege is claimed are defined as follows:

1. An electronic device for managing a user's health, the device comprising:
   a) an enclosure comprising a power source, a processor unit, and a memory, for storing and analyzing data related to health related activity of the user,
   b) one or more extensions;
   c) one or more, sensors for sensing health related activities of the user, the one or more sensors including at least a photo sensor, wherein at least one extension is a utensil;
   wherein the electronic device detects and measures timing of each bite of food with at least the photo sensor to provide feedback to the user on timing of each bite of food.

2. The device of claim 1, wherein the one or more sensors include a sensor selected from the group consisting of at least one of a stretch sensor, a motion sensor, a pressure sensor, a proximity sensor, and a touch sensor, and combinations thereof.

3. The device of claim 1, wherein the one or more sensors include a sensor that records an indication corresponding to a vertical level of the device.

4. The device of claim 1, wherein the one or more sensors include a touch sensor.

5. The device of claim 1, wherein the photo sensor is based on infrared sensing technology.

6. The device of claim 1, wherein the device does one or more of calculating or regulating an energy intake.

7. The device of claim 1, wherein the device detects activity of the user that impacts the user's fitness.

8. The device of claim 1, wherein the the one or more sensors include at least one sensor selected from the group consisting of a pedometer, a sleep meter, a physical apparel activity meter extension, a swimming distance meter extension, a heartbeat sensor extension, and a sweat sensor extension.

9. The device of claim 1, wherein the device does one or more of calculating or regulating an energy expenditure.

10. The device of claim 1, wherein the enclosure is permanently attached to the utensil extension.

11. The device of claim 1, wherein the enclosure Is removably attached to the utensil extension.

12. The device of claim 1, wherein the device communicates with a remote station that processes detected health activity.

13. The device of claim 1, wherein the device is configured to establish a data link with a server to report detected health-related activity of the user to the server for further analysis.

14. The device of claim 1, wherein device is further configured to establish a data link with a server to receive user configuration information related to one or more health-related goals of the user.

15. The device of claim 1, wherein the device is further configured to establish a data link with a gaming device and to provide health-related input during game play.

16. The device of claim 1, wherein the device is further configured to establish a data link to communicate health-related information of the user to a third party associated with the user to manage the user's health.

17. The device of claim 1, wherein the device is further configured to receive notification from an energy balance tracking subcomponent of the health activity detection component and to alert the user at any time of the day that the user is in positive or negative energy balance and should reduce or augment dietary intake and/or physical activity to restore balance.

18. The device of claim 1, wherein the enclosure is further configured to interface with one or more user activity extensions that receive sensory input based on the user's activity or non-activity.

19. An electronic device for managing a user's health, the device comprising:
   a) an enclosure comprising a power source, a processor unit, and, a memory, for storing and analyzing data related to health related activity of the user,
   b) one or more extensions, wherein at least one extension is a utensil,
   c) one or more sensors for sensing health related activities of the user, the one or more sensors including at least a sensor that records an indication corresponding to a vertical level of the device;
   wherein the electronic device detects dietary intake of the user with at least the sensor that records an indication corresponding to a vertical level of the device.

20. The device of claim 1, wherein the device is further configured to adjust health-related goals of the user based on food characteristics.

21. An electronic device for managing a user's health, the device comprising:
   an enclosure comprising a power source, a processor unit, and a memory, for storing and analyzing data related to health related activity of the user,
   b) one or more extensions, wherein at least one extension is a utensil,
   c) two or more sensors for sensing health related activities of the user, the device performing an error correction based on comparison of data collected from the two or more sensors;
   wherein the electronic device correctly detects and measures timing of each bite of food with at least the two or more sensors by performing the error correction to provide accurate feedback to the user on timing of each bite of food.

22. The device of claim 1, wherein the photo sensor senses light intensity variations when approaching or leaving the inside of the user's mouth.

\* \* \* \* \*